(12) United States Patent
Garcia-Bennett

(10) Patent No.: US 9,409,783 B2
(45) Date of Patent: *Aug. 9, 2016

(54) METHOD FOR MANUFACTURING MESOPOROUS MATERIALS, MATERIALS SO PRODUCED AND USE OF MESOPOROUS MATERIALS

(71) Applicant: Nanologica AB, Stockholm (SE)

(72) Inventor: Alfonso Garcia-Bennett, Stockholm (SE)

(73) Assignee: Nanologica AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,130

(22) Filed: Oct. 29, 2013

(65) Prior Publication Data
US 2014/0120021 A1 May 1, 2014

Related U.S. Application Data

(62) Division of application No. 12/867,174, filed as application No. PCT/EP2009/051575 on Feb. 11, 2009, now Pat. No. 8,597,682.

(60) Provisional application No. 61/027,538, filed on Feb. 11, 2008.

(51) Int. Cl.
| | |
|---|---|
| *A61K 8/11* | (2006.01) |
| *C01B 33/26* | (2006.01) |
| *A61K 8/25* | (2006.01) |
| *A61K 8/67* | (2006.01) |
| *A61Q 19/00* | (2006.01) |
| *B01J 20/02* | (2006.01) |
| *B01J 20/06* | (2006.01) |
| *B01J 20/08* | (2006.01) |
| *B01J 20/10* | (2006.01) |
| *B01J 20/20* | (2006.01) |
| *B01J 20/28* | (2006.01) |
| *B01J 20/30* | (2006.01) |
| *B01J 29/03* | (2006.01) |
| *B01J 29/04* | (2006.01) |
| *B01J 35/00* | (2006.01) |
| *C01B 33/12* | (2006.01) |
| *C01F 7/02* | (2006.01) |
| *C01G 3/02* | (2006.01) |
| *C01G 23/04* | (2006.01) |
| *C01G 49/02* | (2006.01) |
| *C01G 51/04* | (2006.01) |
| *C01G 53/04* | (2006.01) |
| *C01G 55/00* | (2006.01) |
| *C02F 1/68* | (2006.01) |

(52) U.S. Cl.
CPC . *C01B 33/26* (2013.01); *A61K 8/11* (2013.01); *A61K 8/25* (2013.01); *A61K 8/67* (2013.01); *A61Q 19/00* (2013.01); *B01J 20/0211* (2013.01); *B01J 20/06* (2013.01); *B01J 20/08* (2013.01); *B01J 20/10* (2013.01); *B01J 20/20* (2013.01); *B01J 20/28083* (2013.01); *B01J 20/28095* (2013.01); *B01J 20/305* (2013.01); *B01J 20/3057* (2013.01); *B01J 29/0308* (2013.01); *B01J 29/041* (2013.01); *B01J 35/004* (2013.01); *C01B 33/126* (2013.01); *C01F 7/02* (2013.01); *C01G 3/02* (2013.01); *C01G 23/04* (2013.01); *C01G 49/02* (2013.01); *C01G 51/04* (2013.01); *C01G 53/04* (2013.01); *C01G 55/004* (2013.01); *A61K 2800/413* (2013.01); *C02F 1/688* (2013.01); *Y02W 10/37* (2015.05)

(58) Field of Classification Search
CPC .......... A61K 8/11; A61K 8/67; Y02W 10/37
USPC ........................ 423/330.1, 325; 424/483, 484
See application file for complete search history.

(56) References Cited

FOREIGN PATENT DOCUMENTS

WO   WO-2007108016 A1   9/2007

OTHER PUBLICATIONS

Cazacu A. et al.: "Dynamic Supramolecular Hybrid and Mesoporous Membranes," Annales de Chimi (Science des Materiaux) Editions Scientifiques et Medicales Elsevier France, vol. 32, No. 2, Mar. 2007, pp. 127-140, XP8120721.
Barboiu, M. et al.: "Ion-Driven ATP Pump by Self-Organized Hybrid Memrance Materials," Journal of the American Chemical Society, 20040322 American Chemical Society US LNKD—DOI: 10.1021/JA039146Z, vol. 126, No. 11, Mar. 22, 2004, pp. 3545-3550.
Gottarelli, Giovanni et al.: "The self-recognition and self-assembly of folic acid salts in isotropic water solution," Helvetica Chimica ACTA, 79(1), 220-34 Coden: HCACAV; ISSN: 0018-019X, 1996, XP002582605.
Gao, C. et al.: "Synthesis and characterization of mesoporous silica AMS-10 with bicontinuous cubic Pn3m symmetry," Angewandte Chemie—International Edition 20060626 Wiley-VCH Verlag DE, vol. 45, No. 26, Jun. 26, 2006, pp. 4295-4298.
Pasqua L. et al.: "Preparation of bifunctional hybrid mesoporous silica potentially useful for drug targeting," Microporous and Mesoporous Materials, Elsevier Science Publishing, New York, US LNKD—DOI: 10.1016/J.Micromeso, 2007.01.045, vol. 103, No. 1-3, Jun. 20, 2007, pp. 166-173.
Liong, M. et al.: "Multifunctional inorganic nanoparticles for imaging, targeting, and drug delivery," ACS Nano, American Chemical Society, US LNKD_DOI: 10.1021/NN800072T, vol. 2, No. 5, Jan. 1, 2008, pp. 889-896.

(Continued)

*Primary Examiner* — Johann R Richter
*Assistant Examiner* — Yanzhi Zhang
(74) *Attorney, Agent, or Firm* — Kim Winston LLP

(57) ABSTRACT

The present invention relates to a new synthetise for the preparation of mesoporous structures including mesoporous materials with chiral morphologies and mesoporous materials with local or surface chirality. The method can be used for manufacturing controlled drug delivery devices, for example for delivery of folic acid, and fluorescent particles.

8 Claims, 9 Drawing Sheets

(56) References Cited

OTHER PUBLICATIONS

Pasqua, L. et al.: "Preparation and cell inclusion of fluorescent folic acid-functionalized mesoporous silica microspheres potentially useful for drug targeting," Studies in Surface Science and Catalysis, Elsevier BV, NL, vol. 1708, Jan. 1, 2007, pp. 1956-1962.

Jinlou Gu et al.: "Organic-inorganic mesoporous nanocarriers integrated with biogenic ligands," Small Wiley-VCH Verlag GMBH Germany LNKD-DOI:10.1002/SMLL.200700311, vol. 3, No. 10, Oct. 1, 2007, pp. 1740-1744.

Ciesla et al., Microporous and Mesoporous Materials, vol. 27, Issues 2-3, 1999, pp. 131-149; published Feb. 1999 by ScienceDirect.com.

| Composition | Template | H₂O | CSDA | Inorganic oxide precursor | Co-Solvent |
|---|---|---|---|---|---|
| Composition 1 | 0.00134moles | 1.66 moles | 0.0016 moles | 0.0072 moles | |
| Composition 2 | 0.00100moles | 1.66 moles | 0.0016 moles | 0.0072 moles | |
| Composition 3 | 0.00201moles | 1.66 moles | 0.0048 moles | 0.0072 moles | |
| Composition 4 | 0.00067moles | 1.66 moles | 0.0016 moles | 0.0072 moles | |
| Composition 5 | 0.00100moles | 0.8 moles | 0.0016 moles | 0.0072 moles | 0.8 moles |

# METHOD FOR MANUFACTURING MESOPOROUS MATERIALS, MATERIALS SO PRODUCED AND USE OF MESOPOROUS MATERIALS

CROSS REFERENCE TO RELATED APPLICATIONS

This application is a Divisional of application Ser. No. 12/867,174, filed on Aug. 11, 2010, which is a National Phase filing under 35 U.S.C. §371 of PCT/EP2009/051575 filed on Feb. 11, 2009, which in turn claims the benefit of the filing date of U.S. Provisional Application 61/027,538 filed on Feb. 11, 2008. The entire contents of application Ser. No. 12/867,174 are fully incorporated herein by reference.

TECHNICAL FIELD

The present invention relates to a new synthetic composition for the preparation of mesoporous structures including mesoporous materials with chiral morphologies and mesoporous materials with local or surface chirality. The method can be used for manufacturing controlled drug delivery devices, for example for delivery of folic acid, and fluorescent particles.

BACKGROUND ART

High surface-area materials with nanoscale dimensions are of special interest in applications where active site mediated chemical reactions play an important role, such as catalytic applications where a high contact area between reactants and catalyst is necessary in order to achieve high yield in a cost-effective manner. There is therefore a large interest in the preparation of nanoscale porous materials, showing increased specific areas with controlled textural (porosity and morphology) properties in the whole range of sizes, i.e. the microscale (below 2 nm) the mesoscale (2-50 nm) and the macroscales (above 50 nm). An example of a porous material is the well known materials such as the crystalline zeolites.

Within the field of porous materials improvements in surface area can speed adsorption rates in for example protein separation devices such as chromatography columns. Control of pore size can increase selectivity for certain products in catalytic reactions. Control of particle size or shape can improve the mechanical stability of a catalyst support as well. Through the discovery of synthesis mesoporous materials of ordered amorphous silica structures, it became possible to make structures with such improved properties. Mesoporous materials are generally referred to materials with silica or other metal oxide compositions displaying sharp pore size distributions in the mesoscale (1.5-50 nm).

The methods rely on self-assembling action of amphiphiles surfactant molecules, which under controlled conditions form ordered micellar systems, as described in U.S. Pat. No. 5,098,684. The surfactant micelles are hereon termed as the pore template or template. A surfactant is a molecule possessing a polar and non-polar group capable of forming micellar structures. Condensation of a suitable silica precursor around micellar species leads to a hybrid organic-silica composite stable through charge matching interactions. The material is rendered mesoporous typically through calcination although routes such as solvent extraction, which enable the recovery of the surfactant template, have also been utilized. It is not a pre-requisite in these preparation routes for the surfactant to be above its critical micellar concentration (CMC). However, in order to have an ordered structure micelles must form at some point during the synthesis process, typically during the hydrolysis and condensation of the silicate precursor.

Micelles may only form when the surfactant concentration is greater than the CMC and the temperature of the solution is above the so-called Krafft temperature. Thermodynamically, micelles form spontaneously as a result of the interplay between entropy and enthalpy. In water, the hydrophobic effect arising from the non-polar group is the driving force for micelle formation. Broadly speaking, above the CMC, the entropic penalty of assembling the surfactant molecules is less than the entropic penalty of "mixing" surfactant monomers with water molecules. Another driving force is enthalpic, such as the electrostatic interactions that occur between the polar parts of the surfactant (typically known as the head-group).

Numerous studies have focused on the synthetic, structural, morphology and compositional control of ordered mesoporous materials.

The preparation of inorganic mesoporous materials as described in U.S. Pat. No. 5,102,643 includes the polymerization of inorganic monomers using a self-assembling amphiphiles surfactant as the template. AU2006231725 describe an alternate synthesis to mesoporous materials; however such methods utilize amphiphilic surfactants as template. Yu Min Sun et al., and references thereof, describes the preparation of mesoporous silica, but once again the use of a surfactant template is a requirement for the formation of ordered pores. KR20070024550 have described the synthesis of mesoporous silica with chiral morphologies using a chiral surfactant template. AU2006231725 describe an alternate synthesis to mesoporous materials; however such methods utilize amphiphilic surfactants as templates.

Only recently has the formation of mesoporous materials with chiral morphologies been reported. Che et al. [Nature, 2004] utilized chiral nematic N-lauroyl-amino acid surfactants and co-structure directing agents (CSDAs) for the synthesis of hexagonal mesophases with chiral morphologies. The role of the CSDA is to facilitate through charge matching the interaction between the organic micellar aggregates and the inorganic silica precursor. This preparation route has subsequently yielded near enantiopure morphologies, however chiral separation and related applications have not been efficiently achieved due to the pore geometry and the pore surface being absent of chirality.

There is a strong desire to provide porous materials capable of separating racemic mixtures, i.e. mixtures of optical isomers. For example, the drug bicalutamide, an oral non-steroidal anti-androgen used in the treatment of prostate cancer, shows enhanced activity towards androgen receptors when the drug is administered in its enantiopure form (R-bicalutamide). It is of commercial interest to develop efficient methods for the separation of such chiral molecules, or for their synthesis using chiral catalysts to their respective enantiopure compounds.

Mesoporous materials are much studied and used in a variety of other applications. In the biotechnology and pharmaceutical sectors the combination of high surface areas and controlled pore geometries can be utilized for delivery of active drug substances that would otherwise require complex, and often not effective and expensive excipients. Controlled drug release from porous structures may result in a reduction of the number of doses and frequency needed to achieve therapeutic results from a drug administration perspective and may solve problems of drug/dose compliance by patients of a prescribed drug regime. Additionally, mesoporous materials show potential applications within this industry to enhance the solubility of poorly soluble drugs.

The solubility of fat-soluble anticancer drugs is a major problem both from uptake and formulation perspectives.

In another application, the encapsulation of enzymes in the pores of mesoporous materials has led to the realization of "heterogeneous" enzyme catalysts, where catalyst recovery and purification are aided from the presence of a porous matrix.

In diagnostics, mesoporous materials have been successfully utilized fluorophores for immunofluorescence and immunohistochemistry, whereby the internal pore volume may be loaded with a fluorescent molecule such as for example molecules of the porphyrin family, fluorescein isothiocyanate and derivatives, or Alexa type fluorescent molecules. This may be attached to the internal walls of mesoporous materials electrostatically or covalently to prevent from leaching out from the porous structure. The external particle surface of a mesoporous material is capable through the introduction of adequate functional groups to support biological conjugates.

Furthermore multiple signals/conjugations may easily be detected through the use of fluorophore loaded particles possessing different stokes shifts. These materials offer sensitive multifunctional detection devices as a result of the high loading capacity of the mesoporous silica particles.

Mesoporous materials are also being investigated for applications in water desalination plants (albeit in combination with polymeric membranes) and as gas separation devices where the combination of functionalized surfaces and pore geometry offers selectivity towards a particular gas, for example in the purification of exhaust gases from NOx and other harmful waste products from catalytic reactions.

Mesoporous materials comprising folic acid may be used as a dietary supplement for the delivery of folic acid and other vitamin B derivatives. Folic acid has many uses in medicine like prevention of neural tube defects (NTDs). Folic acid and other B vitamins help break down homocysteine in the body. Homocysteine levels in the blood are strongly influenced by diet and genetic factors. Dietary folic acid and vitamins B-6 and B-12 have the greatest effects. Several studies have found that higher blood levels of B vitamins are related, at least in part, to lower concentrations of homocysteine. Other evidence shows that low blood levels of folic acid are linked with a higher risk of fatal coronary heart disease and stroke.

Folic acid and derivatives have been associated with a reduction in certain cancer types, such as; colorectal cancer, pancreatic cancer and postmenopausal breast cancer.

Folic acid uptake mechanisms are up regulated in many human cancers, including malignancies of the ovary, brain, kidney, breast, and lung. The folate receptor has a high affinity for folic acid which results in high uptake by up regulated cells, even at low folate loadings on the therapeutic agent. Because of these characteristics, folate conjugation has become a widely used strategy for targeting liposomes, plasmid complexes, nanoparticles, polymer micelles, and other polymer constructs for selective uptake by tumor cells. Folic acid must be internalized into cells via either receptor mediated endocytosis or carrier based uptake mechanisms.

Metal oxide mesoporous materials possessing compositions other than silica which can include nanoparticles of various kinds have a wide variety of potential uses in applications such as catalyst or catalyst supports, capturing gases, water purification, photocurrent switching, photo-cathode in dye-sensitized solar cells, molecular optoelectronic devices or genetic repair in combination.

DESCRIPTION OF THE INVENTION

An object of the invention is to device a method for manufacturing ordered mesoporous materials by a method comprising a non-amphiphilic and non-surfactant template.

Another object of the invention is to device a method for manufacturing ordered mesoporous materials with functional groups attached to inner surfaces of the pores by a method which is non-amphiphilic and non-surfactant template.

Another object of the invention is to device a method for manufacturing an ordered mesoporous material which can have a variety of morphologies including chiral morphologies and chiral porous surfaces.

Another object of the invention is to device a method for manufacturing an ordered mesoporous material which can separate optical isomers.

Another object is to use a mesoporous material manufactured according to the invention for a fluorescent particle containing folic acid or molecules carried by folic acid.

Another object is to use a mesoporous material manufactured according to the invention for controlled delivery of drugs, and especially for controlled delivery of folic acid or molecules carried by folic acid.

The object of the invention is achieved by the methods described in claims 1 and 2.

The present invention allows for manufacturing of mesoporous materials, which can have applications both with the template remaining a part of the material and in a form where the template has been removed.

The invention is based on use of organic molecules capable of forming Hoogsteen-bonded tetrads, pentamers and others supramolecular structures which are formed by a large variety of organic molecules through H-donor and acceptor groups. Such molecules are capable of inducing self-organization to form columnar and hexagonal mesophases, which may then act as an organic template for the hydrolysis and condensation of inorganic oxide precursors with or without the aid of co-structure directing agent, which is a group capable of interaction with the organic template and the inorganic oxide precursor achieving charge matching.

The inorganic precursor can be one or more metal oxide precursor, for example an oxide precursor of Si, Al, Ti, Ni, Cu, Zr, Co, Fe, Ru or Rh.

Co-structure directing agents for the purpose of this invention are typically composed of a basic group such as an amine moiety, bonded to an alkyl spacer which may very in length (propyl, butyl, pentyl, etc) which is in turn is bonded to a alkoxysilane (or titanate, zirconate etc).

The CSDA maybe used on its own or as a mixture of different CSDA. The CSDA may also be composed of a mixture of compositions, for example one CSDA from the group known as the alkoxysilanes and one from the group of alkoxytitanates. The CSDA must be capable of interacting with the pore forming template, either covalently or electrostatically. The CSDA must be capable of interacting with the inorganic oxide precursor.

The invention devices a simple method to prepare ordered mesoporous materials with chiral morphologies and chiral surfaces, with a sharp pore size distribution based on the use of non-surfactant template folic acid and/or derivatives containing a pterin or similar group, such as guanosine and derivatives.

The present invention allows for preparing mesoporous silica nanoparticles with folic acid and/or derivatives whereby a large amount of said molecules can be incorporated in one direct synthesis step into the internal porous surface of the mesoporous material. Furthermore, the type of morphologies produced can include chiral morphologies in the form of fibers or rods and spherical particles varying diameters.

The reaction mixtures may be extruded, dip-coated, spin coated or spray-dried.

DETAILED DESCRIPTION OF THE INVENTION

The present innovation embodies the formation of ordered mesoporous materials using a non surfactant non-micellar template.

The present invention includes a simple method to produce ordered mesoporous structures, with highly ordered mesopores with functionalised groups attached to the internal surface and well defined morphologies.

The present invention includes o a simple method to produce oordered mesoporous materials in the absence of amphiphilic molecules of the group comprising: anionic, cationic, switterionic or polymeric surfactants, or any other type of surfactant molecule.

In addition, a method of loading mesoporous silica nanoparticles with folic acid and derivative substances is devices whereby a maximum amount of said molecules can be incorporated in one direct synthesis step into the internal porous surface of the mesoporous particle. Furthermore, the type of morphologies produced can be controlled, with the formation of chiral morphologies resulting from variations in one of the synthesis components.

Novel materials produced show improved folic acid delivery properties, optical properties and chiral separation properties.

Through this invention, a delivery vehicle possessing the highest possible loading of folic acid is produced in one synthetic step, hence there is no need to produce the mesoporous material first, calcine or extract the pore template, and then load the folid acid content.

Moreover, it is possible in one synthetise step to load the active drug candidate, or other functional molecule such as a fluorophore together with the folic acid pore template. This is possible due to the ability of folic acid to interact through $\pi$-$\pi$ type stacking interactions with itself and other molecules. Thus, any drug capable of interacting through $\pi$-$\pi$ interactions with folic acid (or derivatives), may take part in the self-assembly and itself act as a template. Said $\pi$-$\pi$ interactions are referred to here as a stacked arrangement of aromatic molecules, which interact by intermolecular overlapping of p-orbitals in $\pi$-conjugated systems.

The release profile of folic acid and of any drug substance incorporated into the synthesis in the manner described below is considerably decreased as a result of diffusion limitations imparted by the inorganic porous matrix.

The invention relies on the use of organic molecules capable of forming Hoogsteen-bonded tetrads, pentamers and others supramolecular structures which are formed by a large variety of organic molecules through H-donor and acceptor groups. Such molecules are capable of inducing self-organization to form columnar and hexagonal mesophases, which may then act as an organic template for the hydrolysis and condensation of inorganic oxide precursors with or without the aid of co-structure directing agent, which is a group capable of interaction with the organic template and the inorganic oxide precursor achieving charge matching.

Folic acid is one example of such an organic template molecule but other folate derivatives such as; pterin, carboxypterin, 2,4-Diamino-5-bromomethylpyrimidine, N-[4-{[(2-methyl-4-amino-5-pyrimidyl)methyl]amino~benzoyl]-L-glutamic acid, guanosine monophosphate, N-[4-{[(2,6-diamino-4-hydroxy-5-pyrimidyl)methyl]amino~benzoyl]-L-glutamic Acid, 5¢-tert-butyl-dimethylsilyl-2¢,3¢,-di-Oisopropylidene, derivatives of guanosine and others may be used provided that they contain groups capable of forming tetramers or larger supramolecular structures via hydrogen bonding and $\pi$-$\pi$ stacking interactions.

Folic acid is composed of a pterin group, chemically and structurally similar to guanine, conjugated to an L-glutamate moiety via a p-amino benzoic acid (FIG. 1). The L-glutamate group of folic acid has a pKa value of 8.3 and hence will be deprotonated and negatively charged above a said pH value.

Examples of co-structure directing agents that may be suitable for the present innovation include the groups known as alkoxysilanes, alkoxytitanates, alkoxy zirconates, such as for example: 3-aminopropyltriethoxysilane, 3-(Trimethoxysilyl) propyl methacrylate, (3-Glycidyloxypropyl)trimethoxysilane, 3-amino propyltrimethoxysilane, [1-(2-aminoethyl)-3-aminopropyl]trimethoxysilane, 1-[3-(Trimethoxysilyl)propyl]diethylenetriamine, N-(2-aminoethyl)-3-amino propyltrimethoxysilane, N-trimethoxysilanepropyl-N,N,N-trimethylamoniumcloride, 3-[2-(2-aminoethylamino)ethylamino]propyltrimethoxysilane, ureidopropyltrimethoxysilane, 3-isocyanato propyltriethoxysilane, 3-cyanopropyltriethoxysilane and allyltrimethoxysilane.

The CSDA's maybe used on its own or as a mixture of different CSDA's. The CSDA may also be composed of a mixture of compositions, for example one CSDA from the group known as the alkoxysilanes and one from the group of alkoxytitanates. The CSDA must be capable of interacting with the pore forming template, either covalently or electrostatically, and the CSDA must be capable of interacting with the inorganic oxide precursor. This is a requirement if ordered mesoporous materials are to be formed, and limits the use of CSDAs. Tetraethyl orthosilicate and tetramethyl orthosilicate, are examples of inorganic oxide precursors suitable for the formation of ordered mesoporous materials, but others may include titanium (IV) ethoxide, titanium(IV) butoxide, Titanium(IV) isopropoxide, titanium(IV) (triethanolaminato)isopropoxide solution, aluminium isopropoxide. Non-alkoxide inorganic oxide sources such as metal salts may in addition be used provided they interact with the co-structure directing agent.

An example of manufacturing of a mesoporous material includes the following steps:

(A) Dissolving a template with or without other pore forming agents in a medium that promotes the hydrolysis of at least one metal oxide precursor (see step C).

(B) A step which includes dissolving an additive chemical substance where said chemical substance has the primary role of assembling of pterin groups in the template via Hoogsteen type interactions and as secondary role of interaction with on the one hand the acid moieties of the template and on the other hand the condensing metal oxide precursor.

(C) Mixing the solution with at least one metal oxide precursor.

(D) Solidifying the mixture through for example a sol-gel process under conditions where hydrolysis and condensation of said metal oxide precursor may occur.

(E) An optional step of removing at least a part of the solution by solvent extraction and/or evaporation drying and/or calcination to form the porous material.

Step A

Dissolution of the template molecule can be conducted under aqueous conditions but not excluding non-aqueous solvents. The molar ratio of template molecule to water as exemplified by the use of folic acid, (FA:H$_2$O), can be varied from 0.1:1 to 0.001:1, but better structural order is achieved in the range between 0.0015:1 and 0.003:1. The mixture is stirred at a temperature between 4° C.-100° C. that allows the pore forming template to be homogeneously mixed under an appropriate amount of time.

At this stage other co-templates such as surfactants or morphology controlling agents or pore expanding agents such as amino acids or mixtures of the above may be added, but these are not necessary to achieve ordered porous material or to control the morphology.

The addition of a mineralizing agent such as alkaline compounds (for example sodium hydroxide) or compounds capable of lowering the pH may be added, but this is not necessary in order to form ordered porous materials. The optimum pH in order to form ordered mesoporous structures is between 6-13, and preferably between 8-10. The pH may vary depending on the selection of template, CSDA, and inorganic oxide precursor.

A mixture of templates may also be used for example a mixture of Folic acid and deoxyguanosine-5'-monophosphate, which both are capable of forming interactions to form cholesteric and hexagonal phases.

Molecules that may interact with the folic acid or be carried by the template such as active pharmaceutical products or fluorophores may be added at this stage.

Inorganic salts which stabalise the formation of tetramers by the template (such as potassium salts) may also be added at this stage but are not necessary in order to form an ordered mesoporous material.

Step B

Step B involves adding a chemical substance or substances to the solution. The chemical substance may also promote or effect the formation of Hoogsteen-type interactions between pterin or similar groups within the template through a variation of pH, see FIG. 1. An example of such a molecule is aminopropyl triethoxysilane, APES. The ratio APES:FA may vary from 0.02:1 to 1:1, whilst an optimum material is achieved with ratios varying between 0.2:1 and 0.8:1. The mixture is stirred at a temperature between 4° C.-100° C. that allows the substances to be homogeneously mixed under an appropriate amount of time. The amount of APES added at this stage may have a direct effect on the morphology of the final product and the rate of hydrolysis and condensation of the inorganic oxide precursor added in STEP C and D.

Step C

The solution is mixed with at least one metal oxide precursor. Suitable metal oxide precursors may be formed from any oxide of; silica, alumina, titanium, nickel, copper, cobalt, iron, nickel, ruthenium and rhodium. The silicon alkoxide Tetraethyl Orthosilicate, (TEOS) is especially preferred in this case. If TEOS is used in this step the TEOS:$H_2O$ ratio is preferable between 1:100 and 1:400. TEOS is added to the solution under vigorous stirring at a temperature which may vary between 4° C.-100° C. and kept in those conditions for at least 10 min, in order to homogenize it.

Step D

Solidifying the mixture can be made by a sol-gel transition. The conditions have to be chosen so as to induce the sol-gel transition of the inorganic oxide precursor. This can be done by controlling the amount of thermal energy per gram solution and per unit time which are applied to the reacting (hydrolysis and condensation steps) inorganic oxide precursor until the sol gel transition occurs. The amount of energy applied to the solution during the first three hours is between 0.1 and 10 Joule per minute and gram solution, and preferable between 0.5 and 3 Joule per minute and gram solution. This can be done by keeping the solution in an appropriate sealed vessel at a temperature between 40 and 120° C. preferable between 60 and 80° C., for at least 6 hours, but maybe as long as 10 days. The temperature has to be chosen according to the thermal conductivity of the vessel and the amount of reacting solution. If the vessel and solution have a lower temperature than the surrounding, heat from the surrounding is transferred to the vessel and solution by conduction. A hydrothermal treatment may also be necessary to promote condensation. This is conducted at temperatures between 60-100° C., for a period of between 5 hours and 5 days. The preferred temperature in the case of the use of Folic acid is 80° C., due to the decomposition of the pore template at higher temperatures. A hydrothermal treatment is not necessary in order to form an ordered mesoporous material. The length of time of the hydrothermal step may be decrease if a higher temperature is used. After the solidification process has terminated, the materials produced may be recovered by simple filtration.

Alternatively, Step D may be carried out using spray-drying equipment, or a dip-coating equipment, or a spin coating equipment. This is particularly useful if an organic solvent such as ethanol is added during step A.

Step E

This step concerns a method to remove the solvent and organic compounds from the pores without damaging or collapsing the pore structure. This step allows production through solvent extraction (E1) of a porous material with a functionalised surface corresponding to the chemical substance described in Step B and otherwise known as the CSDA. Hence, if in B, APES is used then the internal surface of the ordered porous material after solvent extraction will contain aminopropyl groups. The molar concentration of these aminopropyl groups will depend on the ratio of template-chemical substance (for example FA:APES).

An alternative method for removal of the organic template is calcination of the ordered porous particles at 550° C. (E2), in a stream of air or $O_2/N_2$ gas.

Chiral mesoporous materials produced through the present system show chiral characteristics in the particle shape and the pore systems but also within the internal pore surface due to the inherent chiral organization of pterin groups and derivatives thereof.

Furthermore, since the aminopropyl groups (if APES is utilized in step B) interact electrostatically with the glutamate groups of the template, and said template is chiral then the aminopropyl groups after E1 will posses a chiral arrangement with respect to the pore direction. This is termed here local chirality. The degree of enatiomeric purity of such chiral functional groups will depend on the enantiomeric purity of the template used in STEP A. The materials produced after STEP D may be used without STEP E in applications where the template, for example FA, or an additive such as an active pharmaceutical product or fluorophore is the active substance in the application. Such substances will remain in the final product if this is does not undergo Steps E1 or E2.

Self-assembly of pterin groups in Folic acid (a, b) promoted through the addition of a chemical substance in Step B of the invention described here. Diagram (c) shows how the glutamate groups of FA arrange through a combination of Hoogsten type interactions and π-π type stacking, into a chiral structure which is replicated by the chemical substance in Step B.

FIG. 2

Some typical novel compositions of matter which in accordance to the invention are tabulated

FIG. 3

Low angle XRD patterns of materials prepared under the conditions outlined in claims 1-10. Examples clearly show mesoscale order with typical XRD peaks that may be indexed on the basis of a hexagonal unit cell.

FIG. 4

High angle X-ray diffraction peaks of samples where mixed template compositions have been used owing to the ordered arrangement of stacks of template. At least one peak owing to the arrangement of stacks is observed, which is not to be confused with the broad peak observed between 20-25 degrees in 2theta corresponding to inorganic oxide wall.

FIG. 5

TGA/DTG curves, for material derived after step D in the process described above. Three distinct decomposition weight-loss regions can be observed. Region I (150-250° C.) is associated with the decomposition of freely grafted or surface bound organoalkoxysilane groups derived from the hydrolysis of APES. Region II (250-450° C.) can be associated with the overlapping decomposition of the organoalkoxysilane located within the internal surface and the glutamate component of the folic acid. Region III (450-8000 C) marks the decomposition of the pterin and p-amino benzoic acid. Generally these values occur at higher temperatures than those previously reported for the decomposition of free folic acid. The amount of APES taking part in the supramolecular assembly of folic acid calculated from the TGA/DTG curves of extracted samples is 10.40 wt % and may vary to as much as 30 wt % depending on synthesis conditions. The total weight percentage of the FA template in the as synthesized mesoporous material is hence calculated as 27.53 wt % and may vary to as high as 60 wt % depending on synthesis condition and starting reaction composition. The TGA/DTG data is evidence for the templating action of pterin containing groups.

FIG. 6

Nitrogen adsorption-desorption isotherms recorded on an ASAP2020 Micromeritics instrument. (a) Nitrogen isotherm recorded on calcined and solvent extracted samples show typical profiles for small mesoporous materials, which is not present for the extracted sample. (b) Pore size distribution curves for extracted (circles) and calcined (squares) novel mesoporous oxide materials displaying sharp pore size distributions.

FIG. 7

Figures 1, 2:
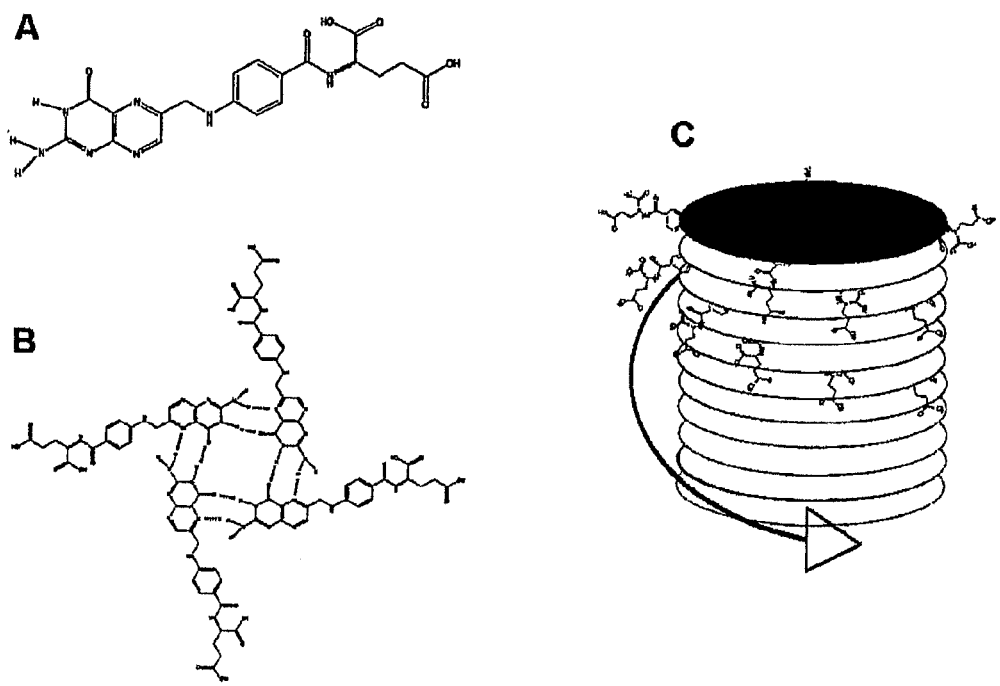
FIG. 1
Figure 3:
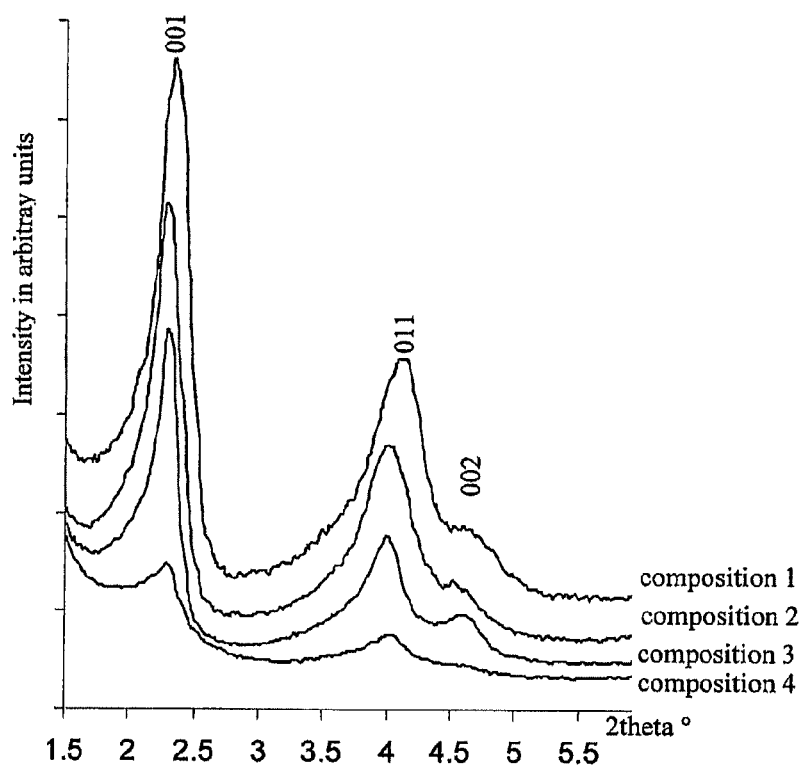
Figure 4:
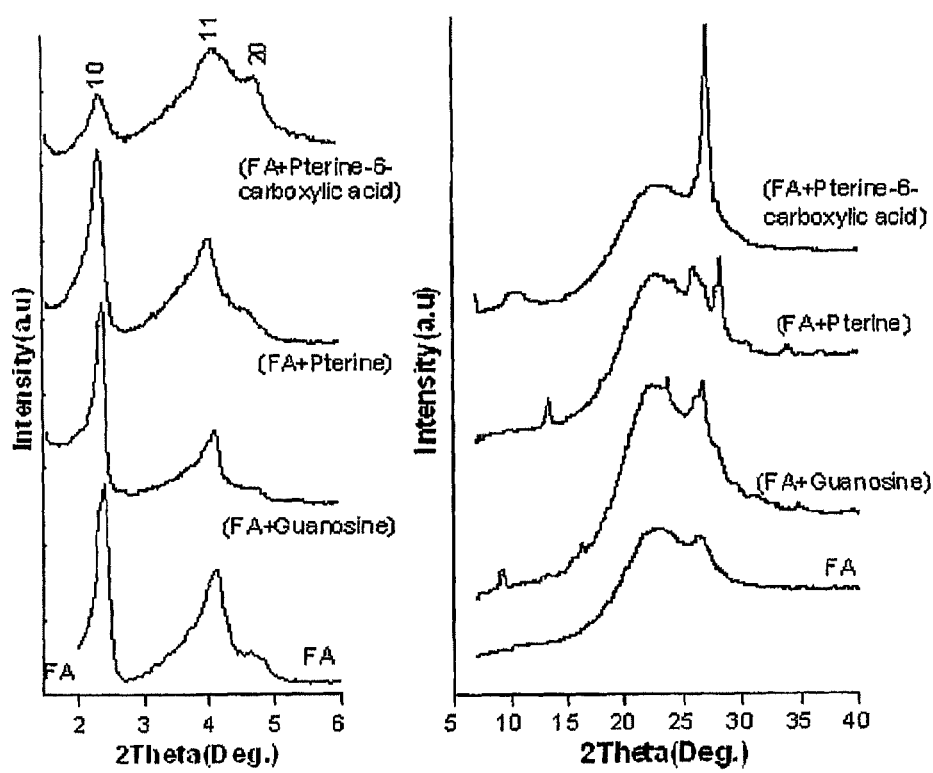
Figure 5:
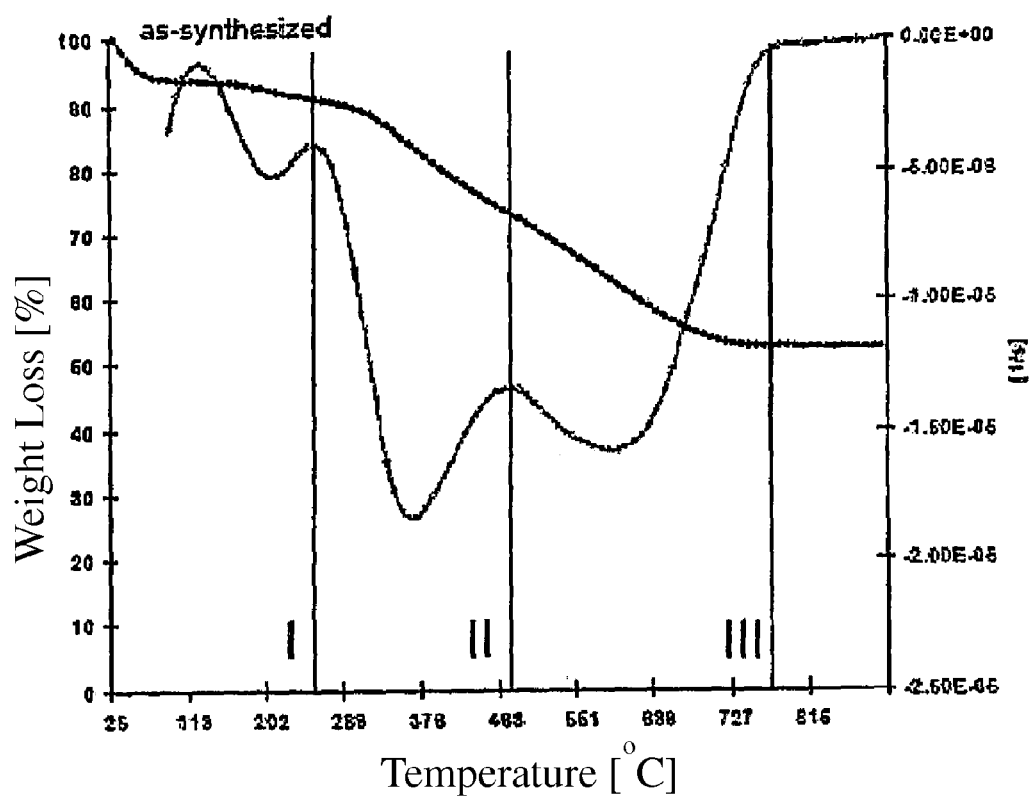
Figure 6:
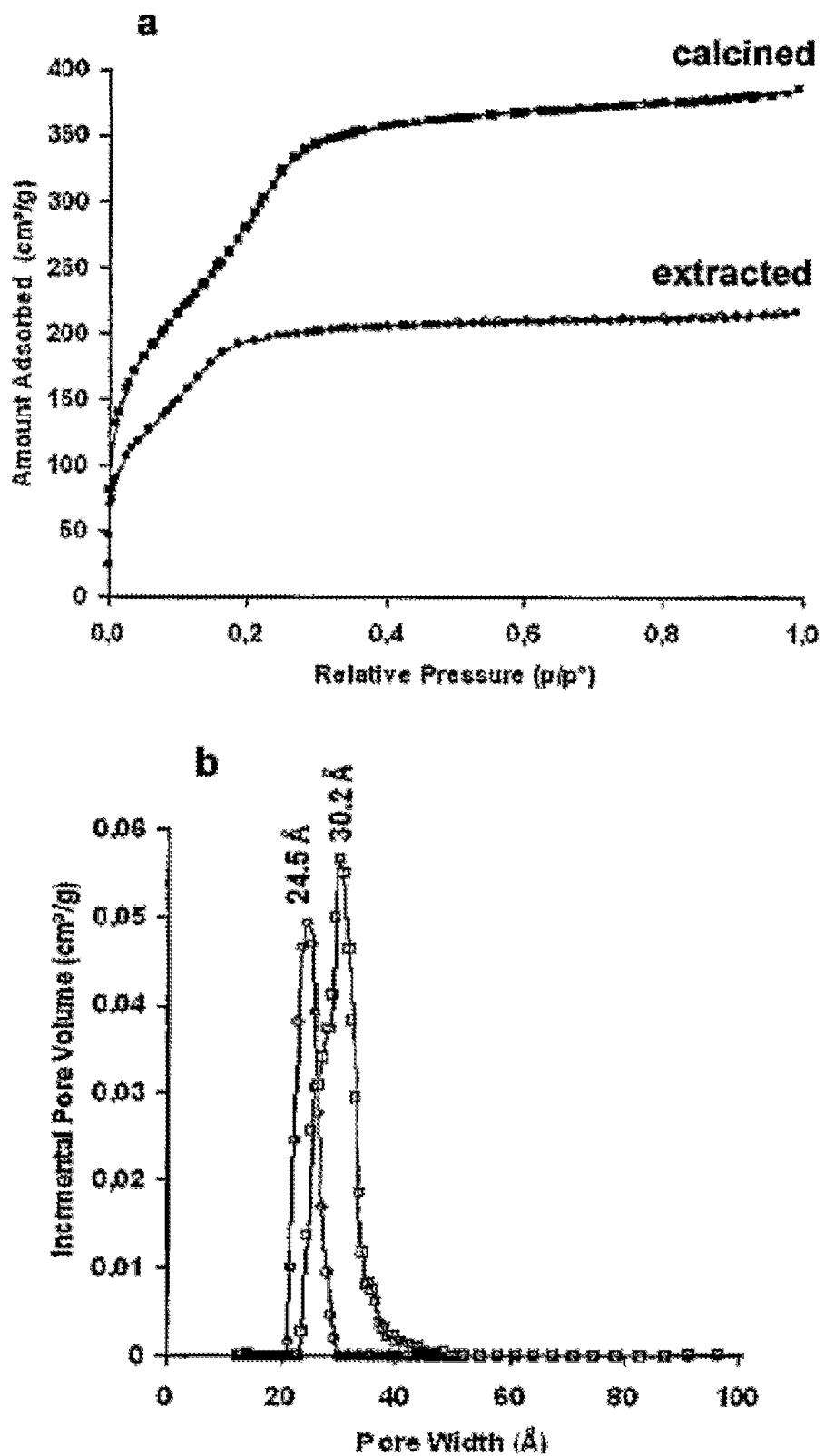
Figure 7:
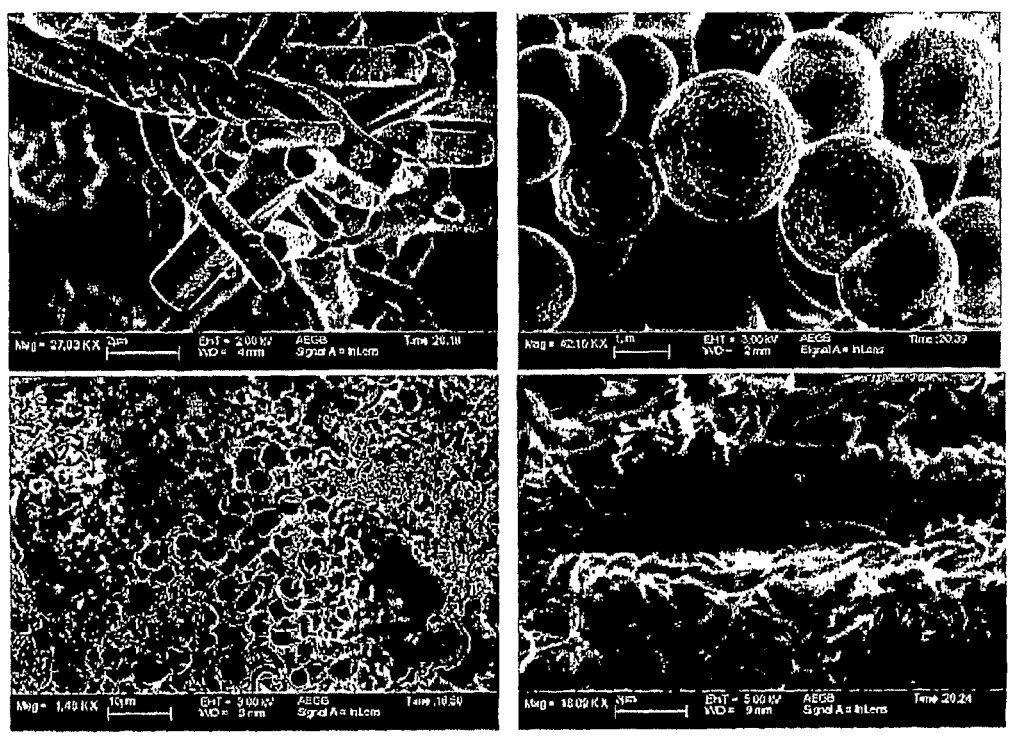
Figure 8:
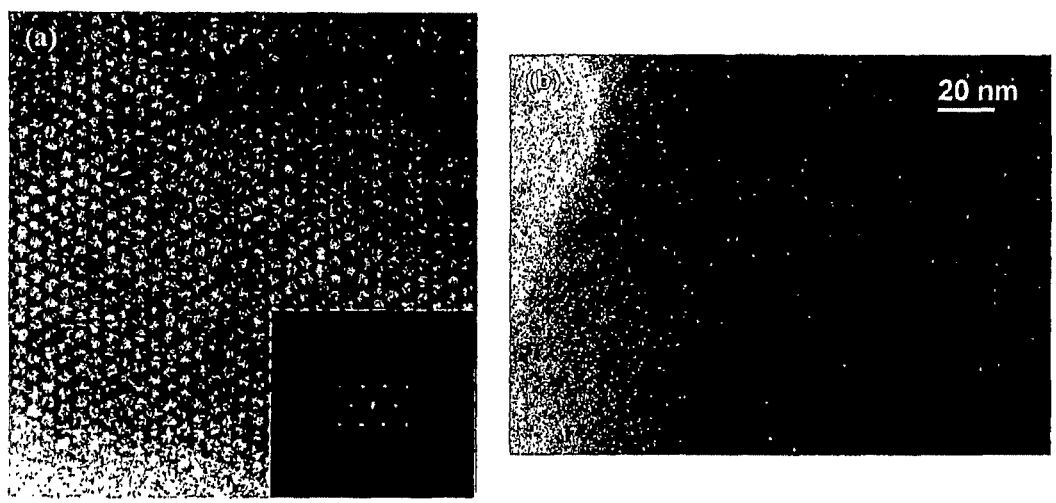
Figure 9:
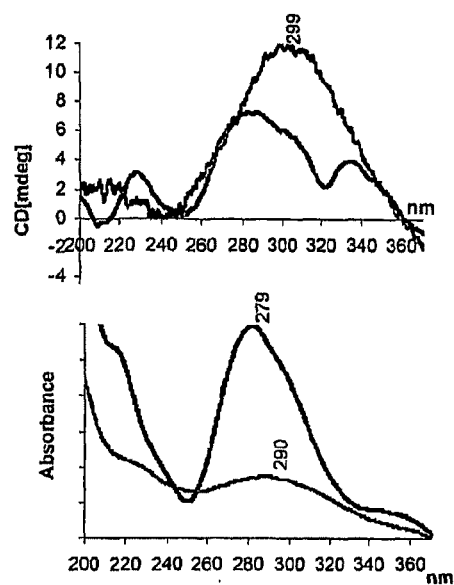
Figure 10:
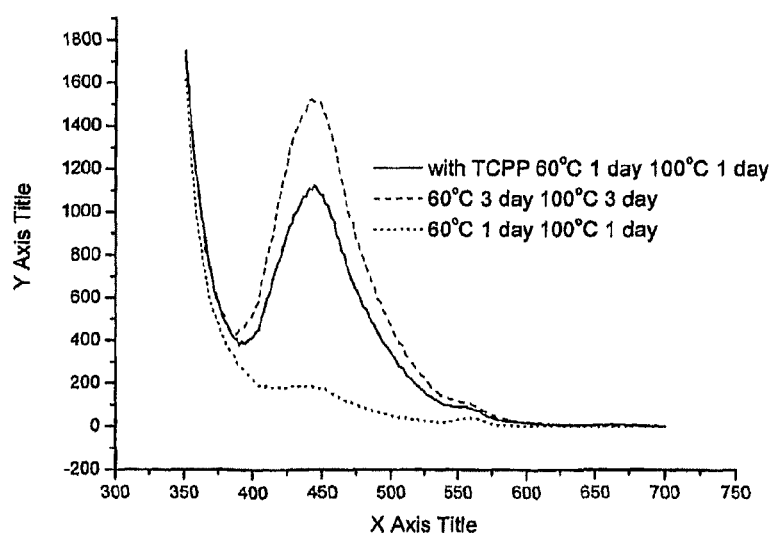
Figure 11:
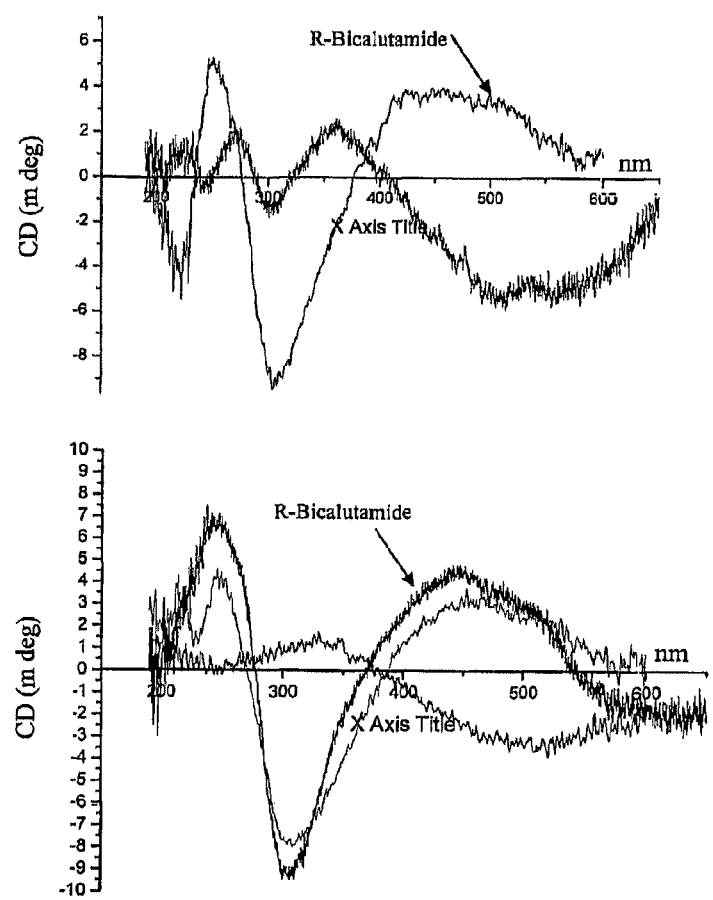

Scanning Electron Microscopy images showing particle morphologies obtained from synthesis compositions 1-5 described in FIG. 2. Rod type particles showing chiral motives are clearly visible. Although in these particles the pitch of the chiral twists is not constant, the direction of this chiral motifs is fixed by the template used.

Other morphologies include spheres, fibres and gyroid particles. Fibres and rod particles vary from 100 nm to a few cm in length depending on synthesis conditions.

FIG. 8

Transmission electron microscopy images of as-synthesised materials prepared in accordance to claim 1, whereby the hexagonal order of the mesopores can be observed directly in the image but is in addition inferred through electron diffraction (a). Image in (b) shows the arrangement of cylindrical pores perpendicular to the electron beam.

FIG. 9

Circular Dichroism (CD) and absorption spectra of folic acid in water at pH=8 (black) and solid state spectra of the as-synthesised mesoporous composition prepared as described in the methods above recorded at room temperature and with concentration of 0.5 wt %. The CD spectra of the solid sample is characterised by a broad positive peak with maxima at approximately 300 nm. This constitutes a peak shift from the expected maxima of folic acid in solution at these conditions (280 nm). It is possible to conclude from the peak shape that the as-synthesised sample retains the chiral imprint from the folic acid template.

The absorbance spectra (curves have been rescaled in the y-axis for ease of comparison) that the maxima is indeed shifted from 280 to 290 nm. This shift in peak maxima is further evidence of the incorporation of the folic acid with in the internal pore space of the mesoporous composition and of the interaction of glutamate moieties with the functionalized wall within the as-synthesised material.

FIG. 10

Fluorescence spectra of as-synthesised mesoporous materials of compositions as described in FIG. 2, prepared at 60° C. (Step C) for a period of between 1 and 3 days and a hydrothermal treatment of 100° C. (Step D) for a period between 1 and 3 days. The spectra of a composition containing using a combination of folic acid and 5,10,15,20-tetrakis (4-carboxyphenyl)porphyrin is also shown as an example of a functional molecule capable of interacting through $\pi$-$\pi$ interactions with the organic template described in Step A.

FIG. 11

Graph in (a) shows Circular Dichroism (CD) spectra of solutions in methanol of a racemic mixture of bicalutamide and of the pure enantiomer R-bicalutamide.

Graph in (b) shows Circular Dichroism (CD) spectra of methanol solutions derived from mixing a specific amount of chiral mesoporous material as described in claim 2-7 (blue line) with a racemic mixture of bicalutamide. The positive spectra observed belong to the single enanotiomer R-bicalutamide. Hence it is possible to conclude that only one enantiomer is adsorbed within the pores of the chiral material described in the present invention. The CD spectra presented here of chiral separation of optical isomers as a result of local chirality.

The invention claimed is:

1. A method for manufacturing ordered mesoporous materials with functional groups attached to inner surfaces of the pores, in the absence of amphiphilic molecules, comprising:
    (A) forming a solution by dissolving a non-amphiphilic and non-surfactant template comprising organic molecules forming Hoogsten-bonded supramolecular structures formed through hydrogen bonding and $\pi$-$\pi$ interactions, wherein the organic molecules of the template comprise folic acid, at a temperature between 4° C.-100° C. and pH between 6-13;
    (B) dissolving an additive substance which is a co-structure directing agents (CSDA) having a primary role of assembling molecular groups in the template, in a molar ratio of from 0.02:1 to 1:1 with respect to the organic molecules of step (A), and at a temperature between 4° C.-100° C.;
    (C) mixing the solution with at least one inorganic precursor, wherein the inorganic precursor is one or more metal oxide precursors selected from the group consisting of Si, Al, Ti, Ni, Cu, Co, Fe, Ru and Rh;
    (D) solidifying the solution by a process where hydrolysis and condensation of the inorganic precursor can occur; and
    (E) removing at least part of the template by solvent extraction to form a porous material.

2. A method according to claim 1, wherein a co-structure directing agent capable of covalent or electrostatic interaction with the pore forming template is added in step A.

3. A method according to claim 2, wherein the co-structure directing agent comprises an amine moiety bonded to an alkyl spacer which may vary in length, and which bond to the inorganic precursor.

4. A method according to claim 1, wherein the metal oxide precursor is one or more of tetraethyl orthosilicate, aluminum isopropoxide and titanium butoxide.

5. A method according to claim 1, wherein the metal oxide precursor comprises silica precursors selected from the group consisting of TEOS and TMOS, and a ratio of silica precursor to template lies between 1:0.001 and 1:0.5.

6. A method according to claim 1, wherein said step (A) is carried out in an aqueous solvent.

7. A method according to claim 6, wherein the molar ratio between folic acid and water ($FA:H_2O$) is in the range 0.001:1 to 0.1:1.

8. A method according to claim 7, wherein the molar ratio between folic acid and water ($FA:H_2O$) is in the range 0.0015:1 to 0.003:1.

* * * * *